United States Patent [19]
Hunsberger et al.

[11] Patent Number: 5,246,425
[45] Date of Patent: Sep. 21, 1993

[54] TROCAR AND CANNULA ASSEMBLY

[76] Inventors: Daniel Hunsberger, 728 Ridge Rd.; Lloyd Detwiler, 37 Daniels Rd.,, both of Sellersville, Pa. 18960; Robert F. Pflug, 40 N. 5th St., Souderton, Pa. 18964

[21] Appl. No.: 948,217

[22] Filed: Sep. 21, 1992

[51] Int. Cl.$^5$ ............................................. A61M 5/00
[52] U.S. Cl. ................................... 604/165; 604/272; 604/274
[58] Field of Search ............... 604/165, 164, 167, 170, 604/272, 274, 273; 606/108, 167, 170, 172, 184, 185; 30/162, 152

[56] References Cited

U.S. PATENT DOCUMENTS

| | | | |
|---|---|---|---|
| 2,882,598 | 4/1959 | Fidelman | 30/294 |
| 4,091,537 | 5/1978 | Stevenson, Jr. | 30/286 |
| 4,230,123 | 10/1980 | Hawkins, Jr. | 128/658 |
| 4,393,587 | 7/1983 | Kloosterman | 30/162 |
| 4,414,974 | 11/1983 | Dotson et al. | 30/162 |
| 4,419,094 | 12/1983 | Patel | 604/93 |
| 4,447,236 | 5/1984 | Quinn | 604/169 |
| 4,473,076 | 9/1984 | Williams et al. | 128/305 |
| 4,491,132 | 1/1985 | Aikins | 128/305 |
| 4,523,379 | 6/1985 | Osterhout et al. | 30/151 |
| 4,535,773 | 8/1985 | Yoon | 604/51 |
| 4,556,059 | 12/1985 | Adamson, Jr. | 128/305.3 |
| 4,601,710 | 7/1986 | Moll | 604/165 |
| 4,654,030 | 3/1987 | Moll et al. | 604/165 |
| 4,716,901 | 1/1988 | Jackson et al. | 128/343 |
| 4,902,280 | 2/1990 | Lander | 604/165 |
| 4,931,042 | 6/1990 | Holmes et al. | 604/164 |
| 5,009,642 | 4/1991 | Sahi | 604/170 |
| 5,066,288 | 11/1991 | Deniega et al. | 604/274 |
| 5,104,382 | 4/1992 | Brinkerhoff et al. | 604/274 |
| 5,127,909 | 7/1992 | Shichman | 604/272 |
| 5,158,552 | 10/1992 | Borgia et al. | 604/274 |

*Primary Examiner*—John G. Weiss
*Attorney, Agent, or Firm*—Logan & Simkanich

[57] ABSTRACT

The present invention provides an improved trocar assembly for use in creating an incision in a patient. The trocar of the present invention includes a unique piercing apex, which eases the insertion process, and an internal tip protector to protect the patient and medical personnel from accidental puncture injuries. The improved tip protector is designed to become fully extended immediately after the leading edge of the trocar enters the patient, thus avoiding many of the operational drawbacks of existing trocar tip protector designs. Additionally, the present invention provides an improved tip protector locking mechanism which is believed to be far simpler and more reliable than existing locking mechanisms.

19 Claims, 5 Drawing Sheets

TROCAR AND CANNULA ASSEMBLY

BACKGROUND OF THE INVENTION

1. Field of the Invention

The present invention relates to trocars and similar devices used in surgical procedures. More particularly, the present invention is directed to an improved trocar and cannula assembly for use in such procedures.

2. Background of the Prior Art

Although there is a long history of employing a variety of tools to assist in creating openings in a human or animal patient during surgery, recent improvements in surgical technology and techniques has spurred renewed interest in methods of establishing and maintaining such openings in a patient.

Traditionally, a sharp trocar instrument has been employed to produce an incision in a patient, which is then often followed by the insertion of a cannula to provide an orifice through which necessary drainage or surgical techniques could be performed. One of the major concerns in introducing a trocar into a patient is that the force of incision often produces a considerable follow-through force which may result in accidental puncture wounds to internal organs.

As a result to this concern, recently a variety of new apparatus have been introduced to attempt to improve upon this basic procedure. One of the major areas of interest has been in attempting to provide an automatic safety shield to surround and protect the trocar tip immediately upon entry into the patient. Examples of such devices are illustrated in U.S. Pat. Nos. 4,535,773 issued Aug. 29, 1985, to Yoon, 4,601,710 issued Jul. 22, 1986, to Moll, 4,654,030 issued Mar. 31, 1987, to Moll et al., 4,902,280 issued Feb. 20, 1990, to Lander, 4,931,042 issued Jun. 6, 1990, to Holmes et al., and 5,066,288 issued Nov. 19, 1991, to Deniega et al. Although these existing devices are definitely a major improvement over previous trocar apparatus, they continued to be plagued with a number of problems.

Foremost among applicants' concerns with the present safety-shielded trocar devices is that the shields do not activate soon enough. In every commercially available shielded trocar known to applicants, the safety shield comprises essentially a tubular unit which is activated to surround the entire outside of the trocar's piercing end upon insertion. Examples of such designs are illustrated in each of the above patents. Even though such shields are generally effective at guarding the trocar's cutting tip, when these units are inserted through the patient's skin tissue the tissue surrounding the external safety shield offers significant resistance and impedes shield activation. As a result, the entire piercing end of the trocar and the shield normally must be fully inserted before the shield can activate. As a result, if extreme care is not exercised the incision force often can follow-through to cause serious internal injury in the instant before the safety shield can achieve a fully extended position.

The use of an external trocar safety shield also tends to present a myriad of other problems. First, the external shield tends to provide an additional impediment to insertion, thus requiring greater incision force and compounding the risk of follow-through injury. Second, the force of the safety shield passing through the skin tissue often results in tearing and other damage at the incision. In addition to needlessly increasing the size of the surgical wound, this also tends to compromise the foundation of a cannula and may lead to undesirable leaks of fluids and gases during the operation. Third, a number of physicians have complained that the recoil from the "snapping" of the safety shield into position at almost the same moment as the trocar insertion tends to disorient them as to the precise location of the trocar after insertion. This results in wasted time and effort to re-orient the trocar and greater risk of internal damage during the period of re-orientation.

Another problem with existing trocar devices is that many employ complicated actuation and locking mechanisms requiring far too much expense and often necessitating costly mated trocar and cannula assemblies. This undermines attempts to recycle those elements (e.g. the cannula) which normally could be sterilized and reused.

Accordingly, it is a primary object of the present invention to provide a trocar apparatus which activates a safety shield with full trocar tip protection before complete insertion of the piercing end of the trocar.

It is a further object of the present invention to provide such a trocar apparatus which is easily inserted and creates a limited incision, thus leaving a minimal surgical wound, providing better stabilization of a cannula or other instruments, and assuring a better seal for gases and liquids during the surgical procedure.

It is another object of the present invention to provide such a trocar apparatus which minimizes recoil from activation of the safety tip protector apparatus so to avoid disorientation of the physician and damage which may be cause by the safety shield itself.

It is still another object of the present invention to provide such a trocar apparatus which has a simple yet effective tip protector locking mechanism, limiting costs while permitting a wider variety of uses, including use with different cannula systems, such as reusable cannula systems.

These and other objects of the present invention will become evident from review of the following specification.

SUMMARY OF THE INVENTION

The present invention provides an improved trocar apparatus for use in a wide variety of surgical procedures on either human or animal patients.

The trocar apparatus of the present invention comprises a trocar, adapted to be inserted through a tubular cannula, and a tip protector assembly housed within the trocar itself. The trocar employs a specially designed conical or pyramidal piercing apex having a contoured sloping side wall. Within the side wall are a series of openings, surrounding the tip of the trocar, through which the tip protector is activated.

In operation, once the tip of the trocar penetrates the patient, but before the entire apex of the trocar is inserted, the tip protector extends through the openings and extends beyond the tip of the trocar to prevent accidental puncture wounds. The present invention avoids many of the problems commonly encountered with existing safety-shielded trocars by assuring that the tip protector is in a fully extended and locked position well before the complete insertion of the trocar into the patient's body. This not only provides a safer trocar apparatus, but also far better feel and control for the physician during the insertion process.

Additionally, the unique contours of the trocar apex design eases insertion and assures minimal incision size.

As a result of the improved trocar piercing apex and the internal tip protector design, the size of surgical wounds are reduced, cannula and other instruments are better supported, and there is a better seal of gases and liquids during operations.

The present invention further employs an improved apparatus for activating and locking the tip protector into position. This apparatus is believed to be simpler and less costly than any other locking devices presently used. Moreover, such activation means permits a wider variety of uses of the trocar of the present invention, including uses with different cannula systems.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved trocar apparatus for use in creating an incision in a patient and establishing an orifice for further medical procedures, such as the insertion of a cannula. It should be appreciated that the present invention is equally applicable to any appropriate surgical procedure, including both medical and veterinary surgery, and the terms used herein, such as "patient," are intended to be read broadly to encompass all such uses.

Referring to FIGS. 1 through 6, the trocar 10 of the present invention comprises a substantially cylindrical shank 12, a piercing apex 14, and a safety shield in the form of a trocar tip protector assembly 16 housed within the shank 12. In the embodiment shown, as is a common application today, the entire trocar assembly 10 is housed within a hollow cannula 18 having an open end 20 and an oppositely disposed housing 22.

Figure 1:
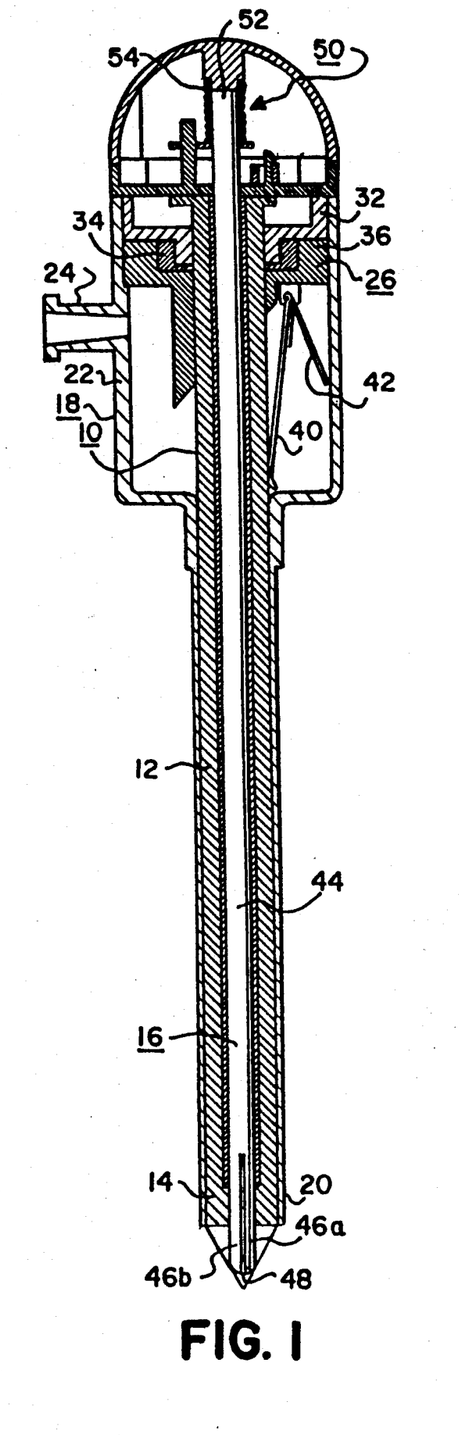
FIG. 1 is cross-section elevational view of a trocar and cannula assembly of the present invention, with a tip protector shown in a retracted position.
Figure 6:
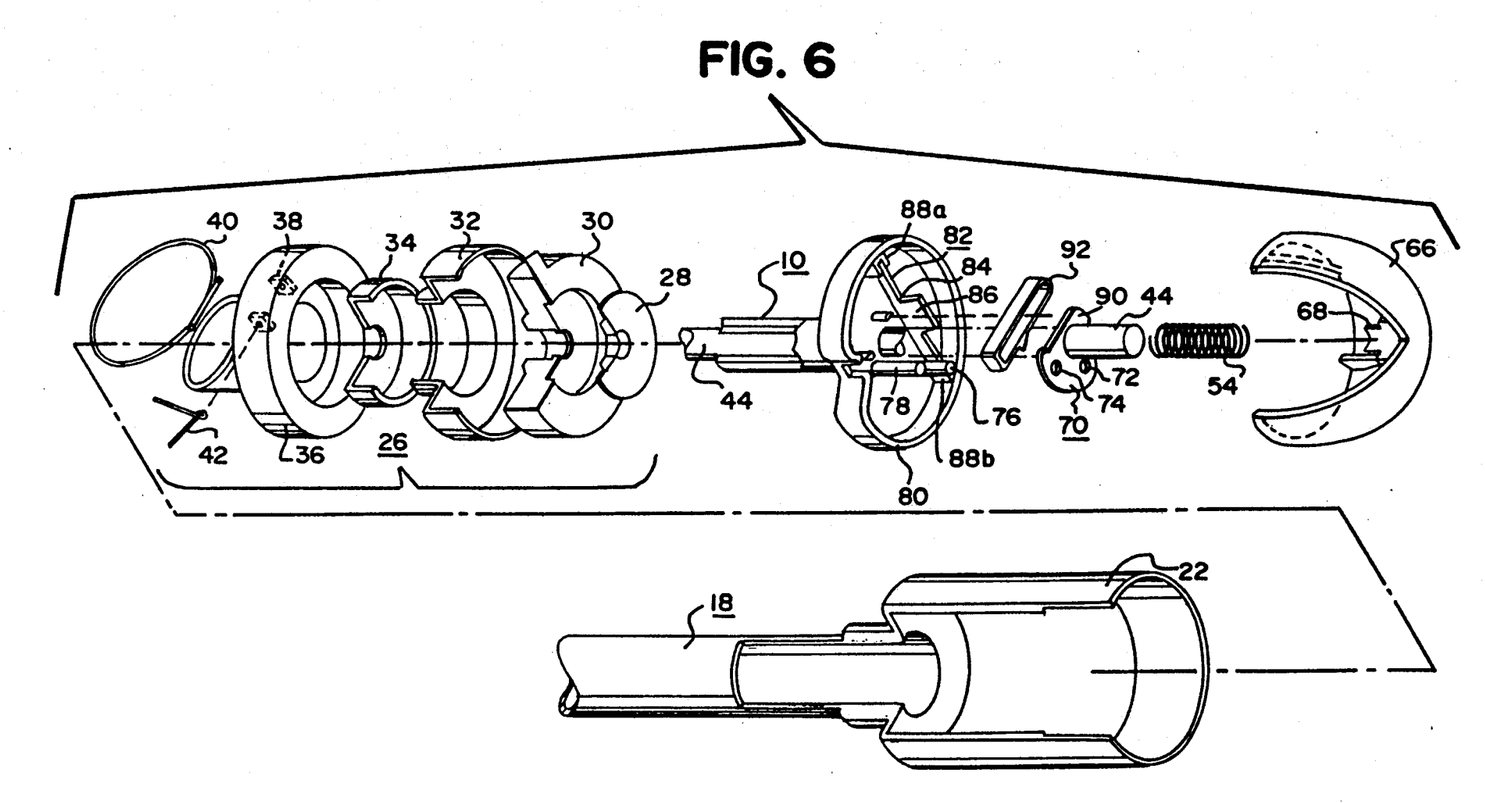
FIG. 6 is an exploded view of the trocar, trocar tip protector actuation and locking mechanism, and cannula of the present invention.

It should be understood that any known cannula 18 may be employed with the present invention. In the embodiment shown, the cannula 18 includes an inlet 24, to permit the introduction of pressurized gases into the patient, and a one-way valve assembly 26, to permit the insertion and removal of the trocar 10 or other instruments through the cannula 18 without significant loss of pressurized gas from the patient. The valve 26 shown comprises: a slightly oblong guide member 28; an elastomer adapter seal 30; a seal retainer 32; a seal 34; a flapper door retainer 36, including a hinge 38 for a flapper door 40; and flapper door spring 42, to actuate the flapper door 40 into a closed position to prevent outward fluid flow through the cannula 18. The guide member 28 and adapter seal 30 are optional elements which may be inserted into the valve for use with thinner instruments once the cannula 18 is installed.

The trocar tip protector assembly 16 comprises an elongated rod 44 having projections 46a, 46b, 46c on its first end 48, and actuation means 50 acting upon its opposite second end 52. The rod 44 may be urged into an extended position by any known biasing means, such as spring 54, an elastomer band or insert (not shown), or similar device.

The piercing apex 14 of the present invention may take any suitable shape, such as pyramidal or conical, and comprises three basic elements: a sharp tip 56; a sloping side wall 58, providing a contoured profile and sufficient surface area to create a smooth transition between the tip 56 and the trocar's shank 12; and multiple openings 60a, 60b, 60c oriented around the tip 56 in the side wall 58. The apex 14 is designed to provide ease of penetration while minimizing damage from the trocar incision. This is accomplished through the cooperation of the tip 56 and the smooth transition to along the sloping side wall 58 to the shank 12. Each of the protrusions 46 of the tip protector 16 is adapted to extend through one of the openings 60 when the tip protector is in an extended position. Although three openings 60 and three protrusions 46 are illustrated herein, it should be understood that the number and shape of these elements can be altered appropriately depending on the desired use of the trocar.

Figures 2, 3:
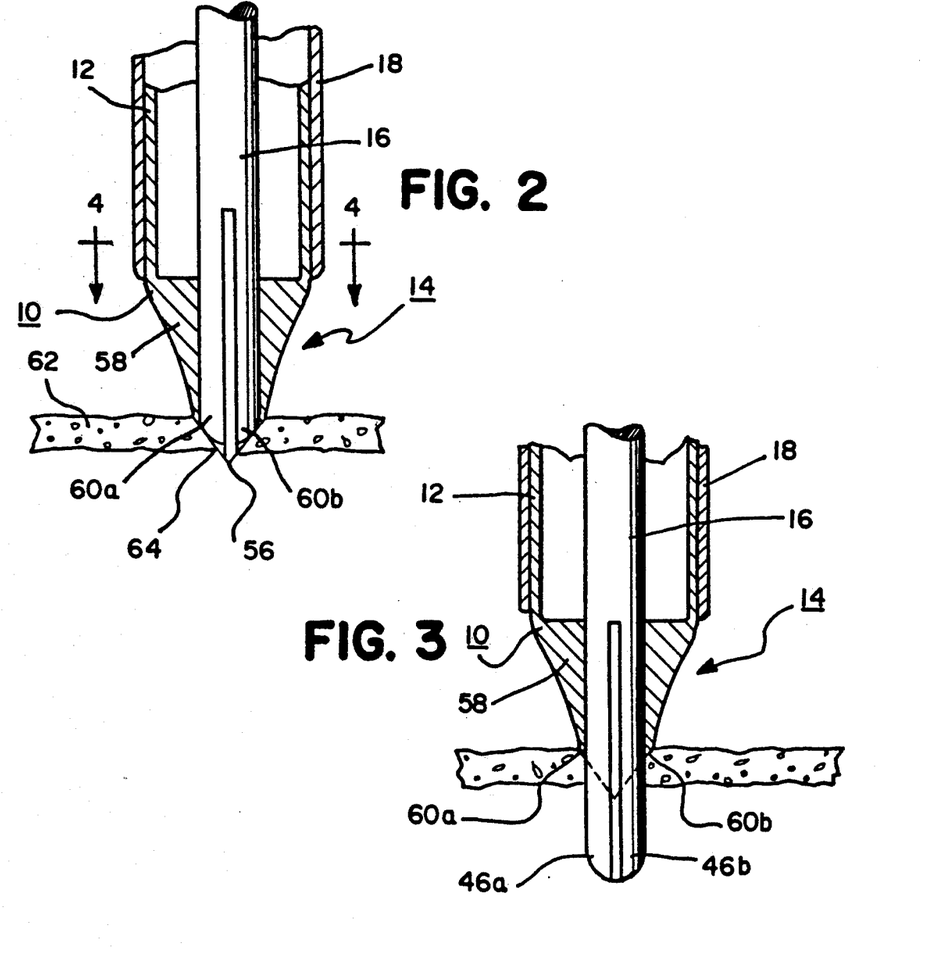
FIG. 2 is an enlarged cross-section view of a piercing apex of the trocar of the present invention, with the tip protector shown in a retracted position as the trocar's tip enters a patient's skin tissue.
FIG. 3 is an enlarged cross-section view of the piercing apex of the trocar of the present invention, with the tip protector shown in an extended position immediately after the tip of the trocar enters the patient's skin tissue.
Figure 4:
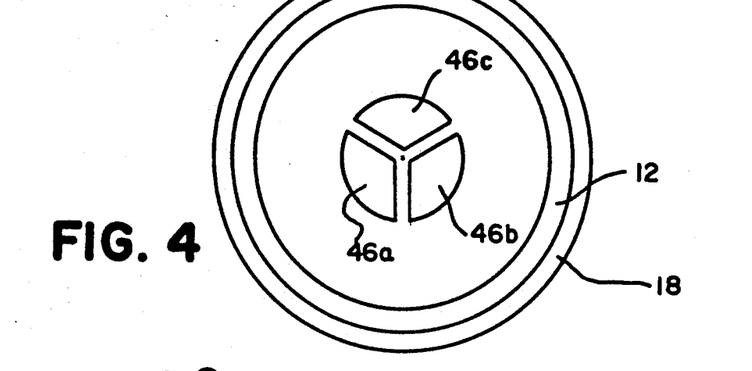
FIG. 4 is a cross-section view along line 4—4 of FIG. 2.
Figure 5:
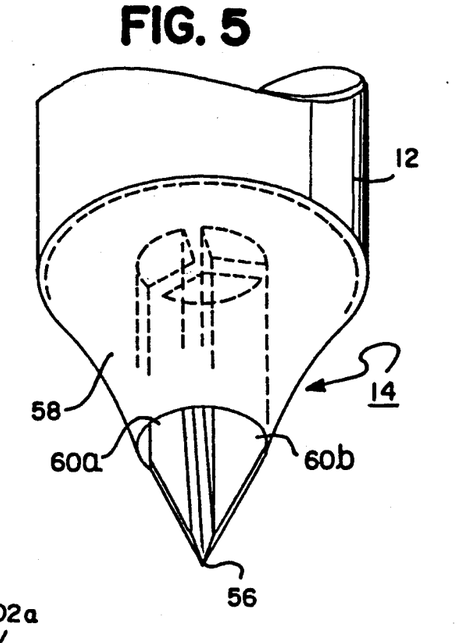
FIG. 5 is a perspective view of the piercing apex of the trocar of the present invention.

The operation of the present invention is illustrated in FIGS. 2 and 3. In its normal resting position the tip protector 16 is in a extended position, such as is shown in FIG. 3, extending through the openings 60a, 60b and protecting tip 56. When the trocar is placed against a patient's skin tissue 62 and pressure is applied, the tip protector is withdrawn into the trocar, exposing the tip 56 to create an incision 64. The rounded nature of the tip protector cooperates with the tip and the sloping side wall to assure a smooth transition upon insertion.

As is shown in FIG. 3, once the tip has initiated an incision and has passed the patient's body wall, the spring biased tip protector 16 is then actuated into an extended position to protect the tip 56 from accidental puncture of internal organs. Unlike previous safety shields, however, the tip protector 16 of the present invention achieves a fully extended position long before the trocar is fully inserted into the patient. Once the tip protector has extended, the trocar can then be fully inserted without the numerous drawbacks inherent with existing trocar tip protector designs. Further, the combined effect of the present invention's unique piercing apex and the internal tip protector greatly reduces tip protector activation recoil and separates such recoil from the moment of fully trocar insertion—thus providing the physician with better feel and control in the insertion process.

Although the tip protector 16 may be controlled by any form of actuation and locking means, it is preferred that such a mechanism be extremely reliable, but of minimal complexity and cost. The preferred embodiment of such apparatus is shown in FIGS. 6 through 11 housed within a trocar cap 66.

Figure 7:
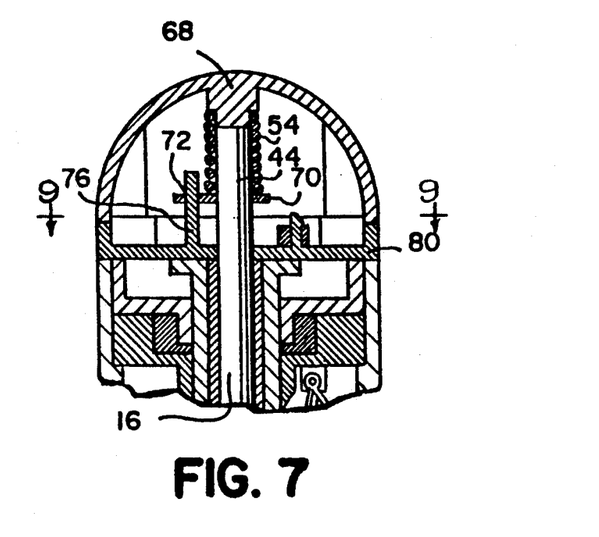
FIG. 7 is an enlarged representation of the trocar tip protector actuation and locking mechanism shown in FIG. 1, with the tip protector in a retracted position.
Figure 8:
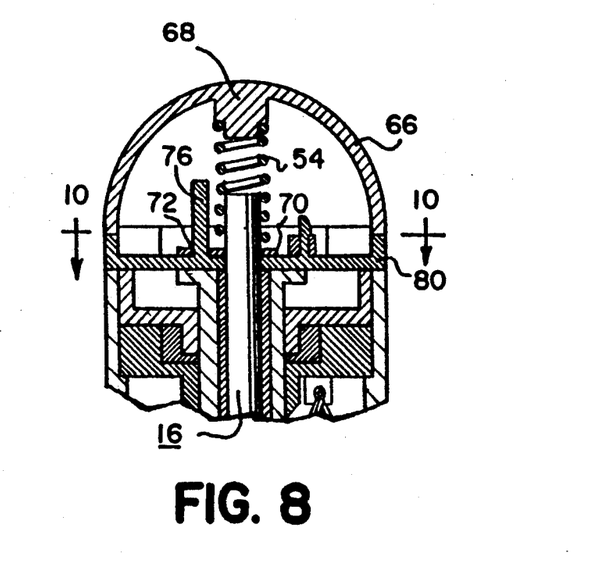
FIG. 8 is the actuation and locking mechanism of FIG. 7 with the tip protector in an extended position.

FIG. 7 shows the tip protector 16 in a retracted position, with the spring 54 being compressed. The spring 54 is mounted around rod 44 and between a spring seat 68 in the trocar cap 66 and a tip protector flange 70 attached to or integral with the rod 44. The compressed pressure of the spring 54 acts upon the flange 70 to urge the tip protector 16 into an extended position when pressure is removed from the projections 46. The extended position of the tip protector 16 is shown in FIG. 8.

To assist in maintaining proper alignment of the tip protector, the flange may be provided with one or more apertures 72, 74 adapted to travel along corresponding guide posts 76, 78 mounted in the trocar cap's base 80.

In order to protect further from accidental puncture wounds within the patient, it is preferred that the tip protector 16 locks into an extended position after it passes through the patient's skin tissue 62. In the present invention this function is accomplished by the interaction of the flange 70 and a stop in the form of a contoured lock spring 82.

The lock spring 82 comprises a flexible horizontal section 84 and a curved vertical section 86 extending therefrom. The lock spring 82 is mounted in the base of the trocar cap by anchoring only the ends of the horizontal section 84 into slots 88a, 88b, leaving a gap beneath the lock spring 82. By constructing the lock spring 82 from a flexible material, such as spring steel or resilient plastic, the vertical section 86 is provided with lateral movement relative to the anchored ends of the horizontal section 84.

Figures 10, 11:
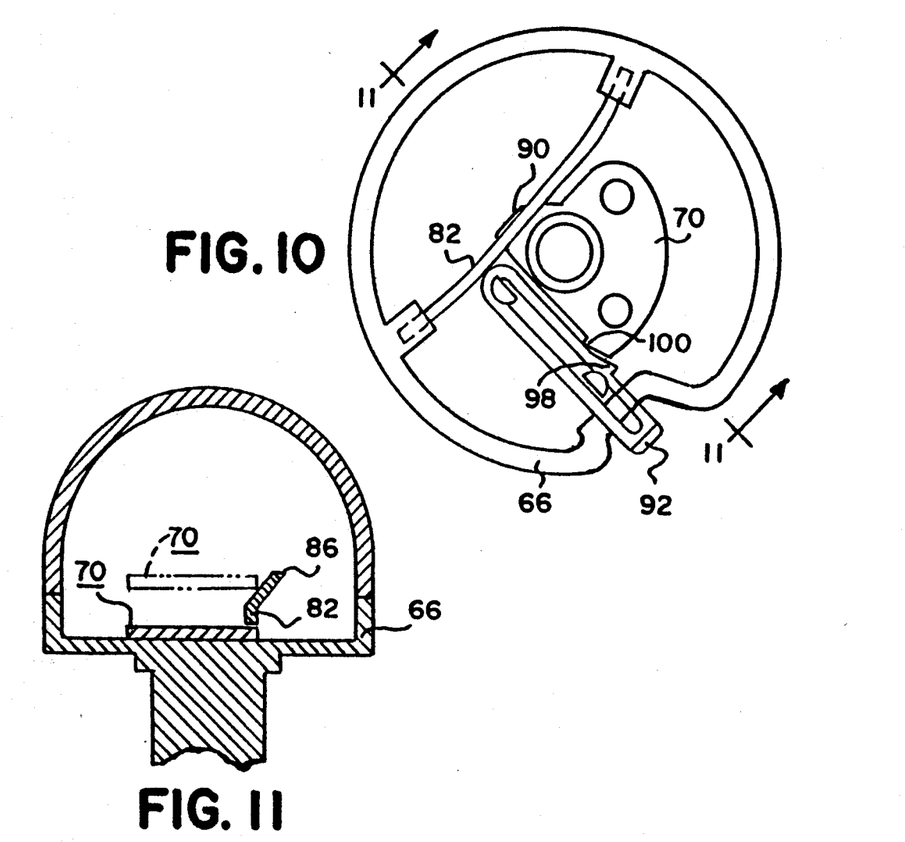
FIG. 10 is a cross-section view along line 10—10 of FIG. 8.
FIG. 11 is a cross-section view along line 11—11 of FIG. 10.

The flange 70 is provided with a lip 90 which is adapted to contact the lock spring 82 and travel down against the vertical section 86, flexing the lock spring out of its relatively straight orientation. When the tip protector is being actuated into a fully extended position, the lip 90 is forced down past the vertical section 86 and into the gap underneath the lock spring 82. The lock spring 82 will then spring back to its straight orientation, trapping the lip 90 under it. This extended and locked orientation is shown in FIG. 10.

Figure 9:
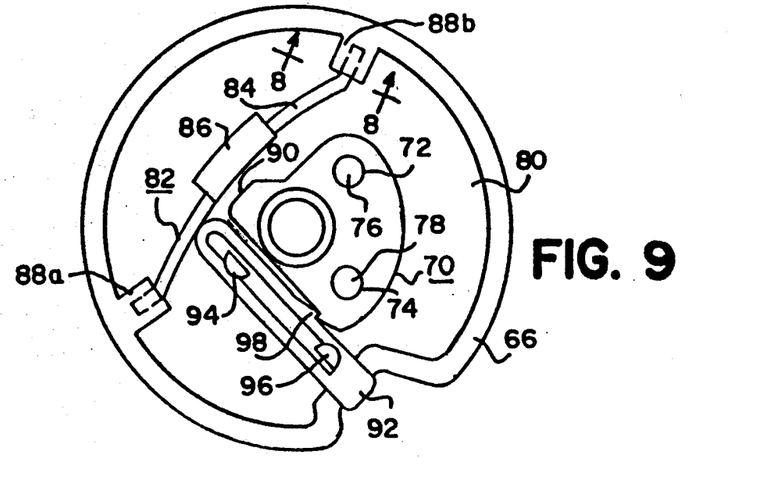
FIG. 9 is a cross-section view along line 9—9 of FIG. 7.

To disengage the locking means of the present invention, a user-activated disengagement slide member 92 is provided in the trocar cap 66. The slide member 92 is mounted in a sliding fashion through a hole in the cap 66 and in contact with lock spring 82. One or more slide retaining posts 94, 96 are provided to aid in maintaining the position of the slide member 92. As is shown in FIG. 9, by pressing the slide member 92, the flange's lip 90 can be freed from under the lock spring 82 to permit the tip protector to travel upward with the assertion of pressure upon the projections 46.

In operation, the lock spring 82 pushes the slide 92 out when the tip protector is actuated in either a fully extended or fully retracted position. In an fully retracted position, flange 90 then contacts vertical section 86, flexing lock spring 82. In this orientation, the slide 92 will remain in the out position due to a slight tension created by slide retaining posts 94, 96 contacting on the side walls of the slot in slide 92. When the tip protector is actuated into an extended position, flange 90 travels down vertical section 86 and lock spring 82 flexes over flange 90 to lock it into an extended position.

To further improve the simplicity of use of the present invention, additional means may be provided to prevent the tip protector 16 from locking into an extended position until after the piercing apex 14 is inserted into a patient. By providing a slide locktooth 98 on the slide member 92 and a complementary a flange locktooth 100 on the flange 70, as is shown in FIG. 9, the lock spring 82 can be retained in an open (i.e. unlocked) position prior to insertion. When the tip protector is retracted in the incision process explained above, the flange 70 is lifted above the slide member 92, disengaging the two lockteeth 98, 100 and allowing the lock spring 82 to return to a straight (i.e. lock-ready) orientation, as is shown in FIG. 10.

The simplicity of the actuation and locking means of the present invention not only leads to greater reliability and reduced manufacturing costs, but it also improves the utility of the present invention. Unlike some existing locking mechanisms which require the interaction between mated trocar and cannula systems, the present invention has been intentionally designed to permit the use of the trocar of the present invention with a variety of cannulae and similar surgical tools without compromising its effectiveness.

Figure 12:
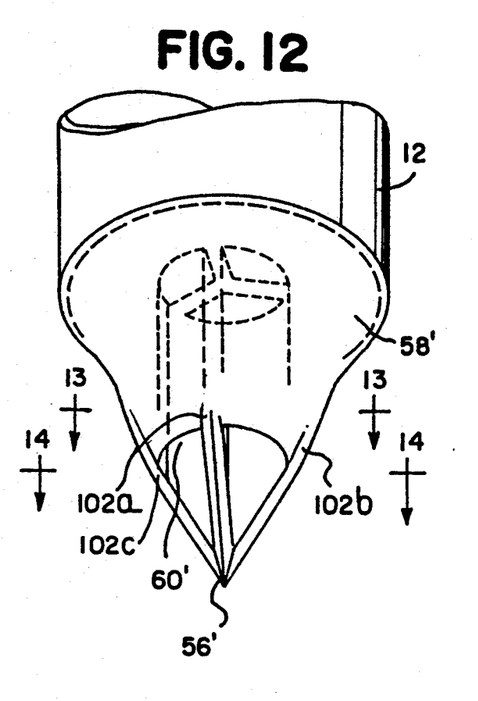
FIG. 12 is a perspective view of another embodiment of the piercing apex of the present invention.
Figure 13:
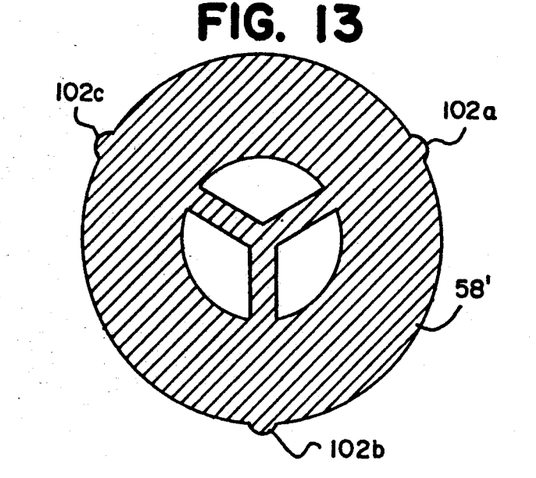
FIG. 13 is a cross-section view along line 13—13 of FIG. 12.
Figure 14:
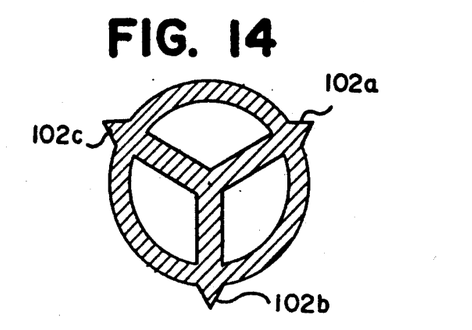
FIG. 14 is a cross-section view along line 14—14 of FIG. 12.

A further refinement of the piercing apex design of the present invention is shown in FIGS. 12 through 14. In this embodiment, one or more bladed ridges 102a, 102b, 102c are provided extending from tip 56' to side wall 58'. Preferably, the ridges 102 are gradually merged into the side wall 58' of the piercing apex above openings 60' and intermediate the tip 56' and the shank 12. This embodiment is believed to provide greater ease in penetration without compromising the other benefits provided by the present invention.

The trocar assembly provided by the present invention is a vast improvement over existing devices. Among the advantages of the present invention are: a tip protector design which assures early activation and reduced risk of puncture wounds; a piercing apex which is easily inserted and creates a limited incision, with minimal surgical wound, better stabilization of a cannula or other instruments, and better seal for gases and liquids during the surgical procedure; a trocar tip protector which minimizes activation recoil so to avoid disorientation of the physician and possible damage which may be cause by the tip protector itself; and a tip protector locking mechanism which is simpler and easier to use than existing mechanisms and permits use with different cannula systems.

Although particular embodiments of the present invention are disclosed herein, it is not intended to limit the invention to such a disclosure and changes and modifications may be incorporated and embodied within the scope of the following claims.

What is claimed is:

1. A trocar and cannula assembly for guarding against accidental puncture wounds of a patient or medical personnel, which comprises a hollow cannula having an open end;

a trocar member adapted to be removably inserted through the cannula so to expose a piercing apex through the cannula's open end, the trocar member having a substantially cylindrical shank terminating in the piercing apex;

the piercing apex comprising a tip, a sloping side wall providing a contoured profile and sufficient surface area to create a smooth transition between the tip and the trocar's shank, and a plurality of openings in the side wall surrounding the tip;

a trocar tip protector housed within the trocar member and adapted to actuate between a retracted and an extended position, the tip protector having a plurality of projections, each projection adapted to pass through one of the openings in the piercing apex, to surround the tip in the extended position; and means to actuate the tip protector into an extended position;

wherein once the tip of the trocar member has entered a patient's body cavity and before the piercing apex has been fully inserted, the tip protector is actuated into an extended position to surround the tip and guard against accidental puncture.

2. The apparatus of claim 1 which includes means to lock the tip protector into the extended position.

3. The apparatus of claim 2 wherein the tip protector comprises an elongated rod having the projections on a first end and the means to actuate the tip protector into an extended position acting upon an opposite second end.

4. The apparatus of claim 3 wherein the means to lock the tip protector into the extended position includes a flange attached at the second end of the tip protector; and a stop which is actuated upon insertion of the piercing apex to engage the flange and lock the tip protector into an extended position.

5. The apparatus of claim 4 wherein the stop comprises a lock spring.

6. The apparatus of claim 5 wherein a disengagement member is provided to actuate the lock spring away from the flange to permit the tip protector to move into a retracted position.

7. The apparatus of claim 6 wherein the disengagement member comprises a sliding lever adapted to push the lock spring out of engagement with the flange.

8. The apparatus of claim 6 wherein means are provided to prevent the tip protector from locking into an extended position until the piercing apex is inserted into a patient.

9. The apparatus of claim 3 wherein the means to actuate the tip protector comprises a spring acting upon the second end of the tip protector.

10. The apparatus of claim 3 wherein the means to actuate the tip protector and the means to lock the tip protector into an extended position are both housed within a trocar cap located at the second end of the tip protector.

11. The apparatus of claim 1 wherein the piercing apex includes bladed ridges extending from the tip to assist in the insertion of the trocar.

12. The apparatus of claim 11 wherein the bladed ridges are gradually merged into the side wall of the piercing apex intermediate between the tip and the shank.

13. A trocar for use in inserting a cannula into a patient, the trocar having a tip protector to protect the patient and medical personnel from accidental puncture wounds, which trocar comprises:

a trocar member having a shank terminating in a piercing apex, the trocar member being adapted to be removably inserted through the cannula so to expose the piercing apex;

the piercing apex comprising a tip, a sloping side wall, and a plurality of openings in the side wall surrounding the tip;

the tip protector comprising a trocar tip protector having a forward and rearward end housed within the trocar and adapted to actuate between a retracted and an extended position, the tip protector having a plurality of projections at the forward end thereof, each projection adapted to pass through one of the openings in the piercing apex, to surround the tip in the extended position, means to actuate the tip protector into an extended position, and means to lock the tip protector into the extended position comprising a flange attached at the rearward end of the tip protector, a lock spring actuated upon insertion of the piercing apex to engage the flange and lock the tip protector into an extended position, and a disengagement member to actuate the lock spring away from the flange to permit the tip protector to be replaced into a retracted position.

14. The apparatus of claim 13 wherein the disengagement member comprises a sliding arm adapted to push the lock spring out of engagement with the flange.

15. The apparatus of claim 13 wherein the sloping side wall is provided with a contoured profile and sufficient surface area to create a smooth transition between the tip and the trocar's shank of the trocar member.

16. The apparatus of claim 15 wherein once the tip of the trocar member has entered a patient's body cavity and before the piercing apex has been fully inserted, the tip protector is actuated into an extended position to surround the tip and guard against accidental puncture.

17. The apparatus of claim 15 wherein the piercing apex includes bladed ridges extending from the tip to assist in the insertion of the trocar.

18. The apparatus of claim 17 wherein the bladed ridges are gradually merged into the side wall of the piercing apex intermediate between the tip and the shank.

19. The apparatus of claim 13 wherein means are provided to prevent the tip protector from locking into an extended position until the piercing apex is inserted into a patient.

* * * * *

UNITED STATES PATENT AND TRADEMARK OFFICE
CERTIFICATE OF CORRECTION

PATENT NO. : 5,246,425
DATED : Sept. 21, 1993
INVENTOR(S) : Daniel Hunsberger et al.

It is certified that error appears in the above-identified patent and that said Letters Patent is hereby corrected as shown below:

Col. 8, line 45: After "and the" delete the word --trocar's--.

Signed and Sealed this

Eighth Day of March, 1994

Attest:

BRUCE LEHMAN

*Attesting Officer*     *Commissioner of Patents and Trademarks*